United States Patent [19]

Larson et al.

[11] Patent Number: 4,697,808

[45] Date of Patent: Oct. 6, 1987

[54] WALKING ASSISTANCE SYSTEM

[75] Inventors: Paul F. Larson, New Orleans; Roy D. Douglas, Kenner, both of La.; Jerrold S. Petrofsky, Beavercreek; Chandler A. Phillips, Tipp City, both of Ohio

[73] Assignee: Wright State University, Dayton, Ohio

[21] Appl. No.: 734,945

[22] Filed: May 16, 1985

[51] Int. Cl.⁴ .............................................. A61N 1/36
[52] U.S. Cl. .............................. 272/70; 128/423 W; 128/783; 128/795; 128/25 R; 623/27; 623/30
[58] Field of Search ................. 128/423 W, 783, 795, 128/25 R, 25 B; 272/70; 623/27, 30, 32

[56] References Cited

U.S. PATENT DOCUMENTS

| 3,083,712 | 4/1963 | Keegan, Jr. ........................ 128/423 |
| 3,204,637 | 9/1965 | Frank et al. ........................ 128/423 |
| 3,344,792 | 10/1967 | Offner et al. ...................... 128/419 |
| 3,449,769 | 6/1969 | Mizen ..................................... 3/1.2 |
| 3,526,007 | 9/1970 | Iuko et al. ............................ 623/58 |
| 4,492,233 | 1/1985 | Petrofsky et al. .................. 128/421 |
| 4,499,900 | 2/1985 | Petrofsky et al. .................. 128/423 |
| 4,569,352 | 2/1986 | Petrofsky et al. ............. 128/423 W |

OTHER PUBLICATIONS

Patent Application Serial No. 561,720, filed Dec. 15, 1983, Petrofsky, "Functional Electrotherapy: Stimulation of the Peroneal Nerve Synchronized with the Swing Phase of the Gait of Hemiplegic Patients", Liberson et al., *Archives of Physical Medicine and Rehabilitation*, Feb. 1961, pp. 101-105.
"Electrical Splinting of the Knee in Paraplegia", Brindley et al., *Paraplegia* 16, (1978-1979), 428-435.
"Programming Six-Channel Electrical Stimulator for Complex Stimulation of Leg Muscles During Walking", Strojnik, et al., *IEEE Transactions on Biomedical Engineering*, vol. BME-26, No. 2, Feb. 1979, pp. 112-116.
"Walking Away from Paralysis", *Discover*, May 1981, pp. 27-29.
"Feedback Control System for Walking in Man", Petrofsky et al., *Comput. Biol. Med.*, 14:135-139, 1984.
"Computer Controlled Walking in the Paralyzed Individual", Petrofsky et al., *Journal of Neurological and Orthopaedic Surger*, vol. 4, Issue 2, Jul. 1983, pp. 153-164.
"Gait Restoration in Paraplegic Patients: A Feasibility Demonstration Using Multichannel Surface Electrode FES, Kralj, et al., *Journal of Rehabilitation R&D*, vol. 20, No. 1, 1983, (BPR 10-38), pp. 3-20.
"The LSU Reciprocation-Gait Orthosis", Douglas et al., *Orthopedics*, Jul. 1983, vol. 6/No. 7, pp. 834-839.
"Functional Electrostimulation of Paraplegics", Holle et al., *Orthopedics*, Jul. 1984, vol. 7/No. 7, pp. 1145-1155.

*Primary Examiner*—Leo P. Picard
*Attorney, Agent, or Firm*—Biebel, French & Nauman

[57] ABSTRACT

A walking assistance system comprising a pair of reciprocating braces and computer controlled stimulation electrodes for stimulating alternating extension of the left and right hips of an assisted person. The braces include left and right leg portions which are interconnected by cables in such a manner as to produce forward motion of either leg when the weight of the person is resting on the opposite leg and the hip of the weight bearing leg is stimulated into extension. The braces are equipped with knee locks which may be unlocked to permit assumption of a sitting position. The cables are also operatively disengaged during sitting.

12 Claims, 20 Drawing Figures

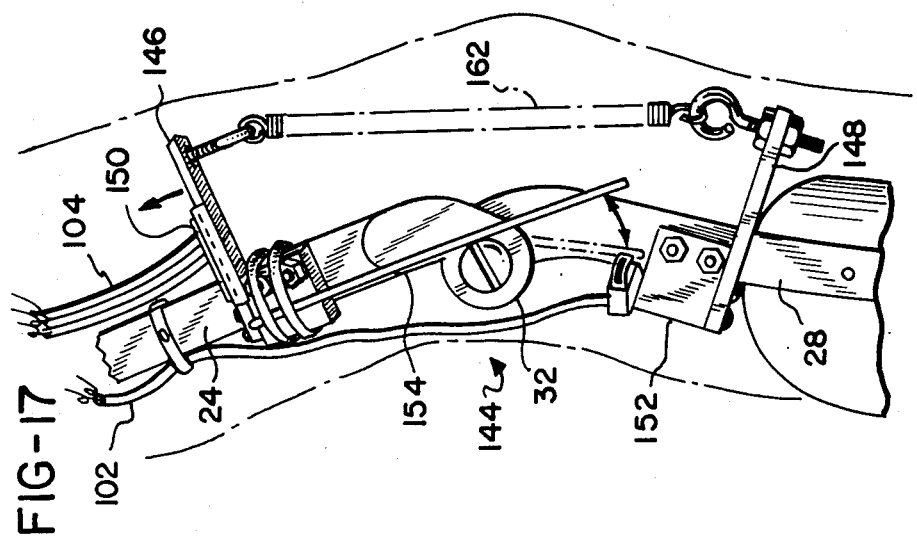
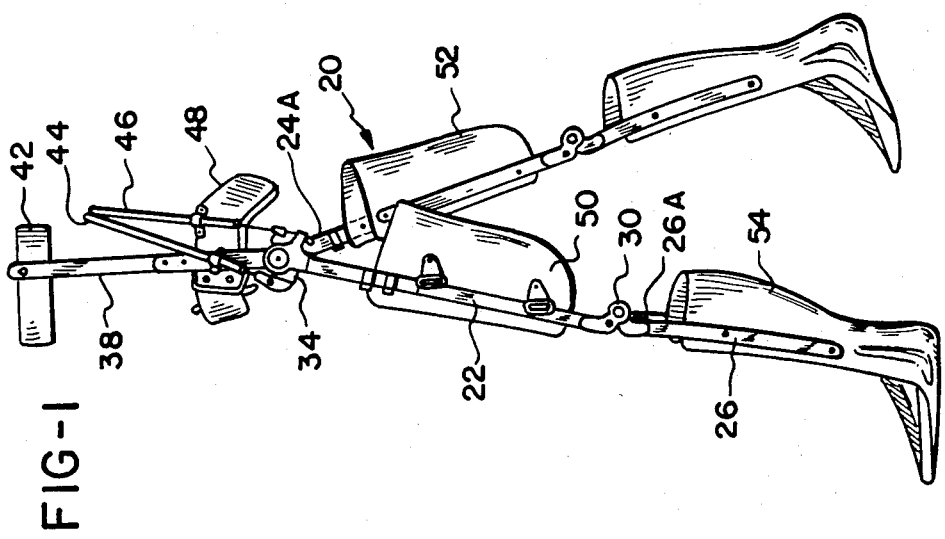

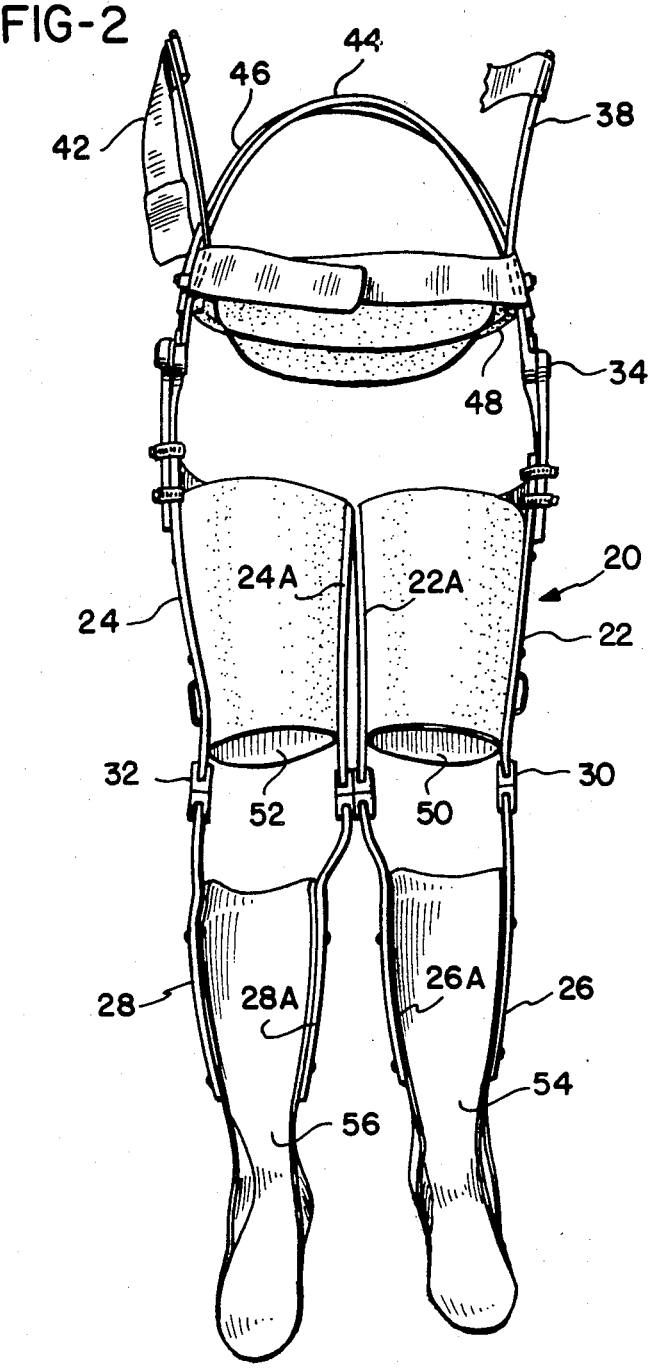

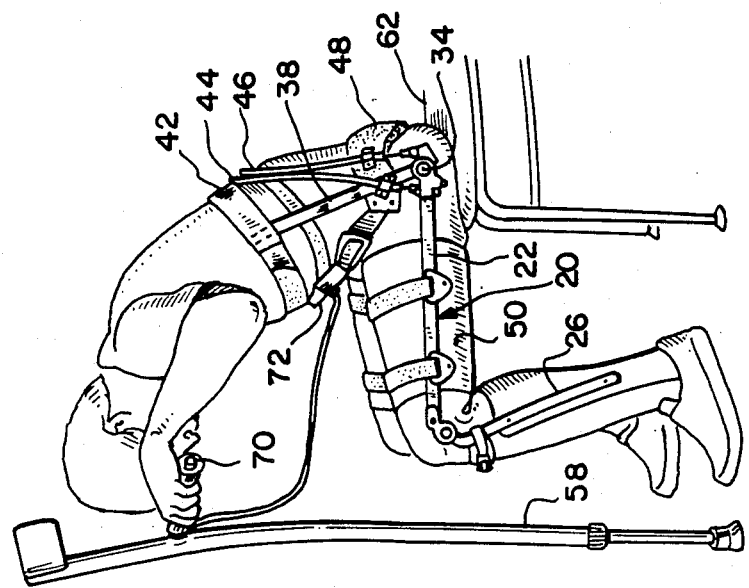
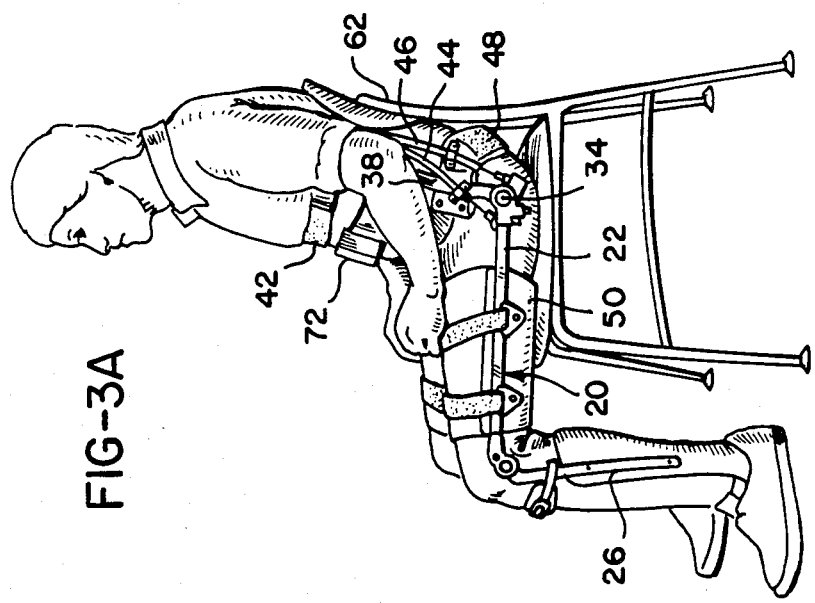

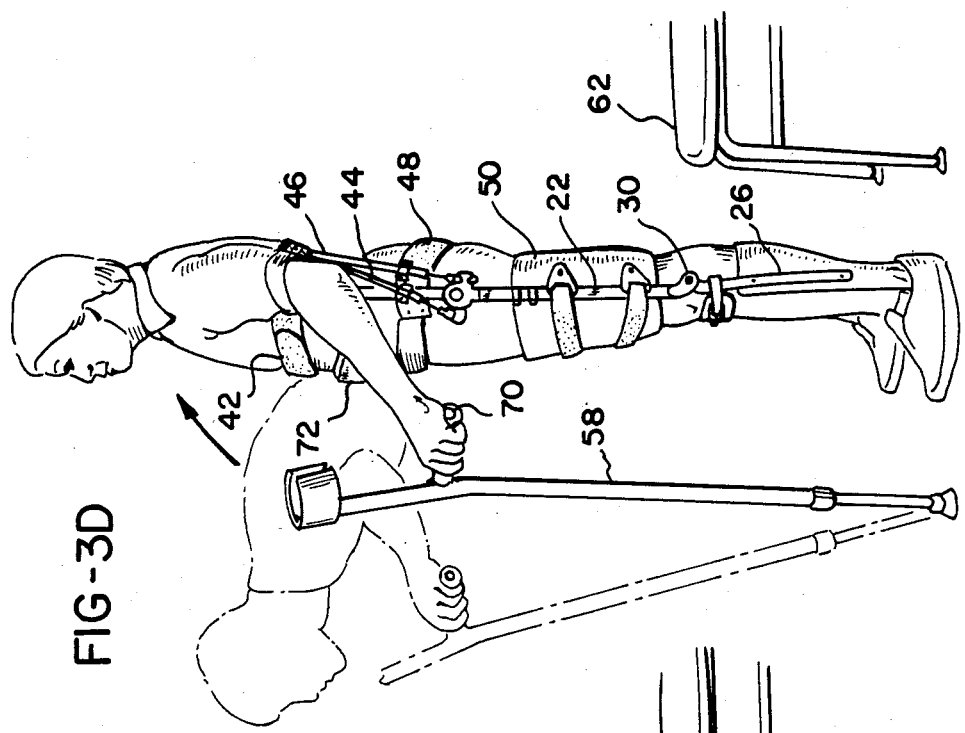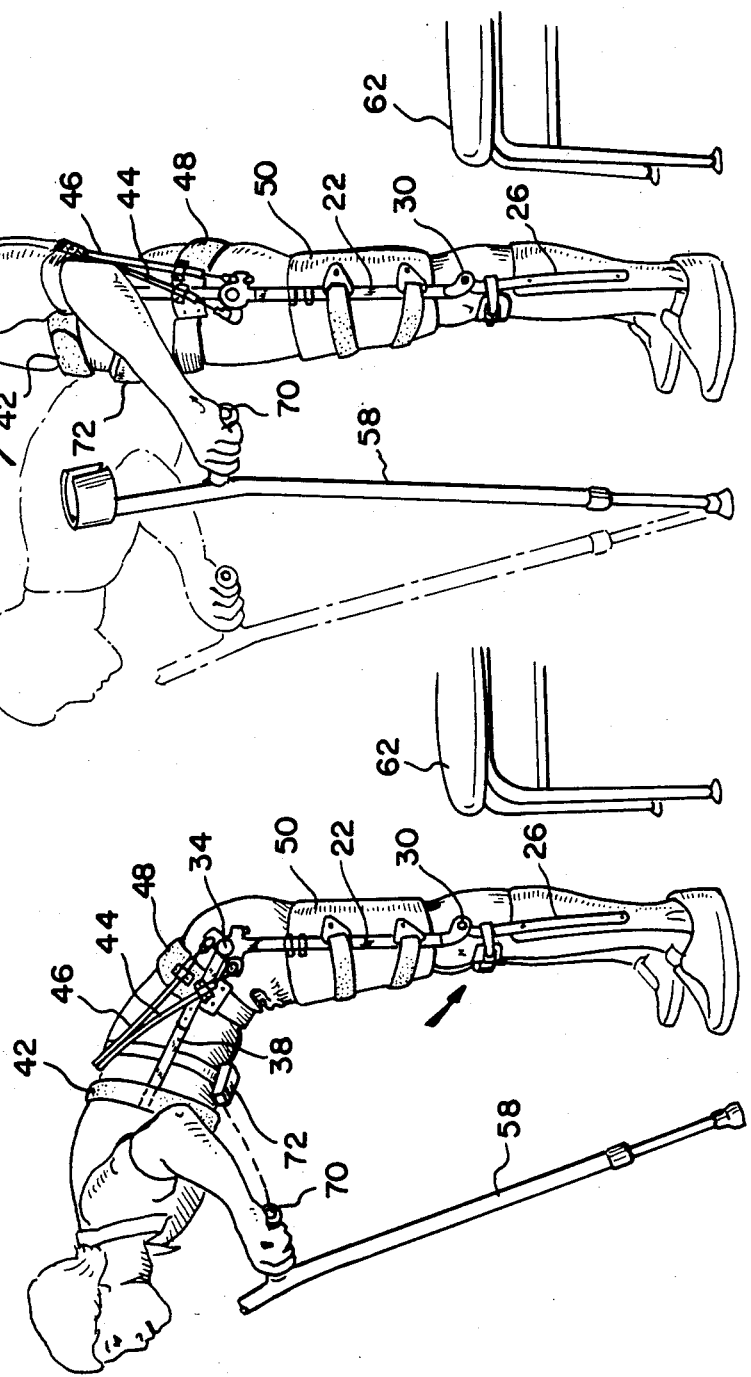

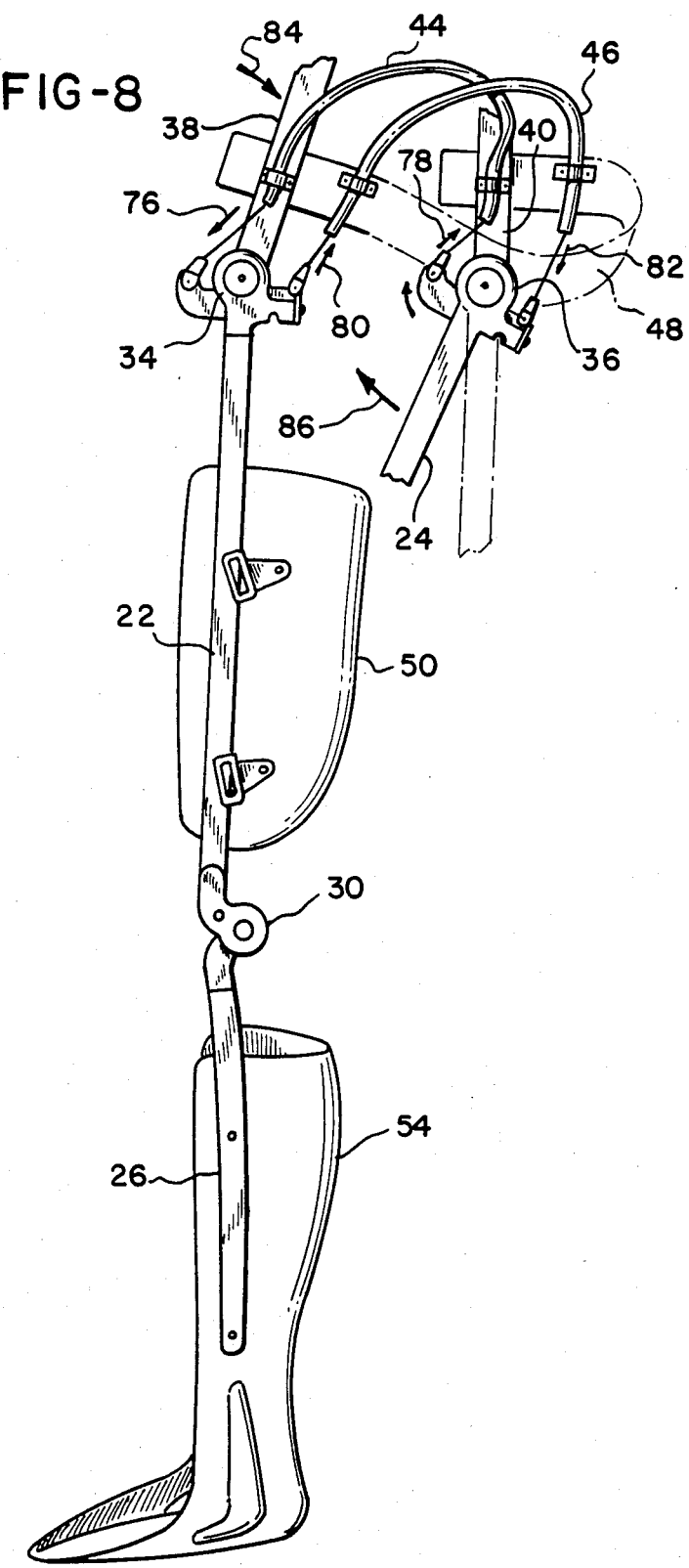

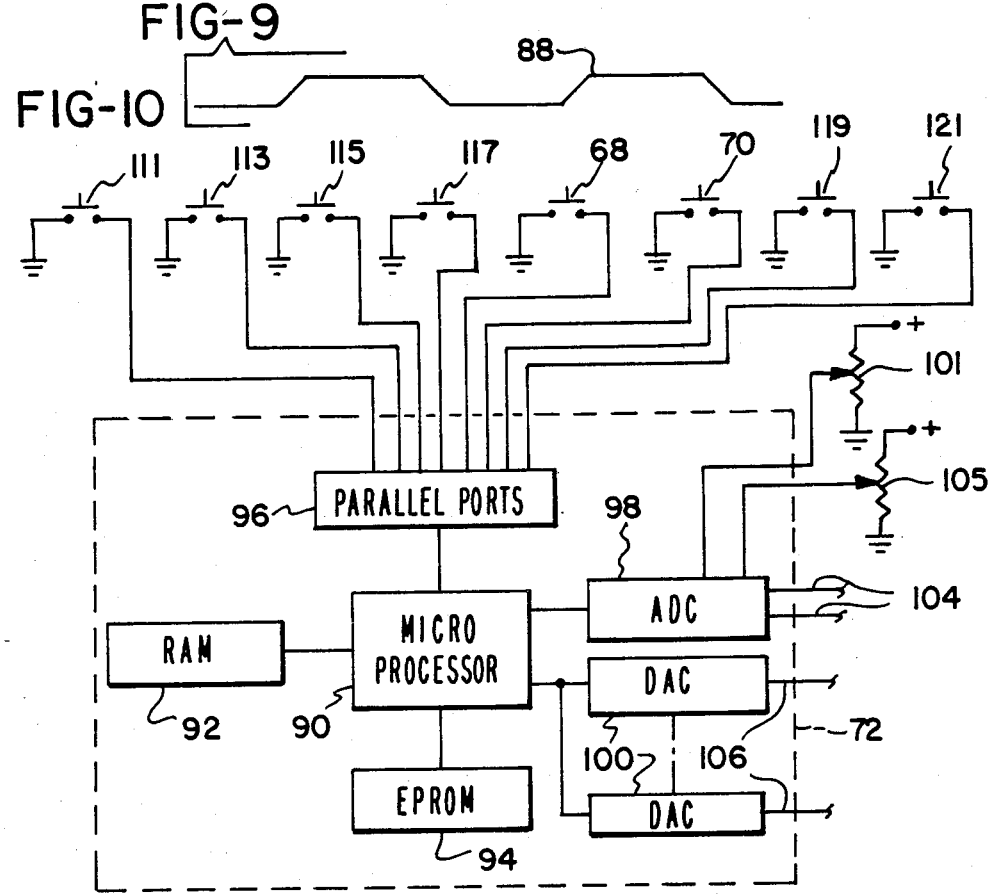
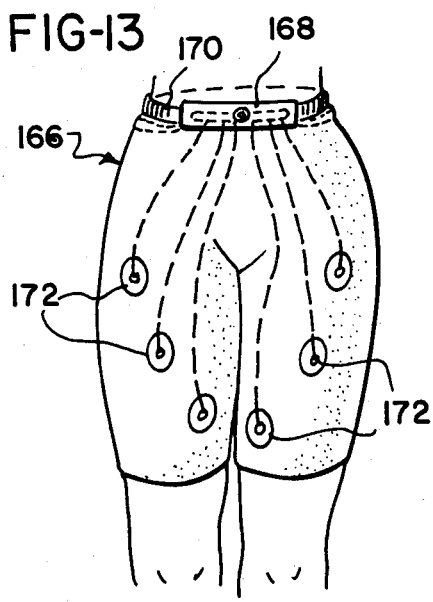
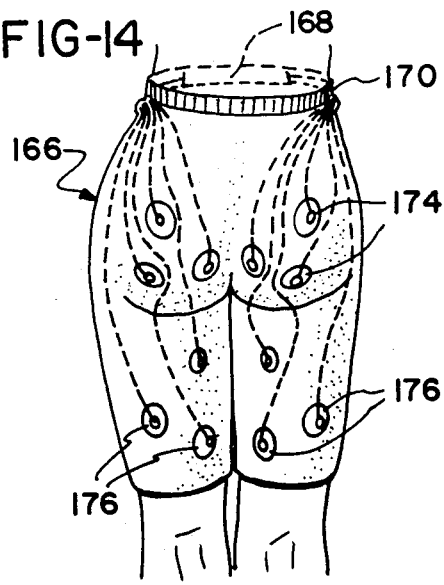

WALKING ASSISTANCE SYSTEM

BACKGROUND OF THE INVENTION

This invention relates to the field of assisted walking for handicapped persons. Such persons may have become paralyzed or partially paralyzed as a result of accident or physiological disorder. Early work in this field concentrated upon walking assistance for persons who were only partially disabled. Typical teachings along that line are set forth in Keegan U.S. Pat. No. 3,083,712, in Frank et al. U.S. Pat. No. 3,204,637 and in Offner et al. U.S. Pat. No. 3,344,792. These references generally teach stimulation of relatively few muscles in a single leg.

Somewhat more recently walking assistance systems have included means for stimulating groups of muscles in both legs as shown in a paper entitled "Programmed Six-Channel Electrical Stimulator for Complex Stimulation of Leg Muscles During Walking," Strojnik, et al. IEEE TRANS on Biomedical Engineering, Vol. BME-26, No. 2, Feb. 1979, pp. 112–116 and in another paper entitled "Gait Restoration in Paraplegic Patients: A Feasibility Demonstration Using Multichannel Surface Electrodes FES," Kralj et al. Journal of Rehabilitation R&D, Vol. 20, No. 1, 1983 (BPR 10-38) pp. 3–20. These systems generally assist walking by stimulating the leg muscles on an open loop basis. That is, stimulation command signals are not adjusted in accordance with measured observations of leg movement.

Stimulated walking under full closed-loop computer control is taught in a paper entitled "Feedback Control System for Walking in Man," Petrofsky et al. Comput. Biol. Med. 14:135–149, 1984 and in a paper entitled "Computer Controlled Walking in the Paralyzed Individual," Petrofsky et al., *Journal of Neurological and Orthopaedic Surgery*, Vol. 4, Issue 2, July 1983, pp. 153–164. The systems described in the Petrofsky et al. papers utilize stimulation devices of the general type described in Petrofsky et al. U.S. Pat. No. 4,492,233. While such systems have been successfully tested, they are extremely complex and have produced walking only for relatively short distances under controlled conditions.

Electrical stimulation has also been used to produce swing-gait type walking. Such walking is accomplished with the aid of crutches. In practicing this technique a standing position is achieved with the body weight resting on the crutches. Then the knee extension muscles and the hip extension muscles are stimulated to enable the legs to support the body weight. Once stimulated standing has been achieved, the crutches are extended forwardly. The person's weight is then shifted to the upper body through the crutches, and the two legs are then swung forwardly to a new weight bearing position. It is apparent that such a walking gait is quite unnatural and very tiring to the upper body muscles. A typical application of this type is described in a paper by Holle et al. entitled "Functional Electrical stimulation in Paraplegics," *Orthopedics*, July 1984, pp. 1145–1155. Such systems have enabled walking for only relatively short distances.

Another technique for assisting handicapped persons to walk utilizes reciprocating braces as described in a paper entitled "LSU Reciprocating Gait Orthosis", Douglas et al. *Orthopedics*, 6:834–839, 1983. The Douglas paper describes an orthosis which supports both legs through an interconnected pair of cables. This system is used by handicapped persons without electrical stimulation of any type. The cables link the hips so that shifting of the weight and tucking of the pelvis causes the hips to initiate a walking gait. These braces have proven quite successful in allowing gait restoration in children and adults with cerebral palsy, MS, and a number of other neuro-muscular disorders. For spinal cord injured patients, the reciprocating braces offer stability and balance. However, for spinal cord injured patients with total paralysis there is a great deal of difficulty in both standing and sitting as well as in walking because power must come totally from the upper body muscles. Further, the lower body muscles are not used during walking with these braces, so there is no prevention of muscle atrophy and bone demineralization.

It is therefore seen that there is a need for an improved walking assistance system for handicapped persons.

SUMMARY OF THE INVENTION

In accordance with this invention, a walking assistance system is provided by stimulating the hip muscles of a handicapped person to operate a pair of reciprocating leg braces. The leg braces configured to restrict the legs to forward and rearward movement and are interconnected in such a manner as to cause forward movement of a nonweight bearing one of the braces in response to stimulated extension of a weight bearing opposite hip of the handicapped person. A control device is provided so that the handicapped person may stimulate extension of either hip while placing his weight on that hip. This causes forward motion of the brace supporting the opposite leg. A pair of crutches, a walker or the like may be provided for balancing assistance during walking.

In the preferred embodiment, the braces are provided with releasably locking knee joints and detachably connected hip cables to facilitate assumption of a sitting position. Movement from a sitting position to a standing position is achieved by coordinated stimulation of the hip extension muscles and the knee extension muscles. The knee joints are locked in place and the hip cables are connected prior to commencement of walking.

Backward walking is the reverse of forward walking and is produced by placing the weight on one hip and stimulating extension of the opposite hip. Sitting is achieved by stimulating the knee extension muscles and the hip extension muscles to support the body, detaching the hip cables and ramping down the muscle stimulation signals. The knee joints unlock automatically during the sitting sequence.

Preferably the knee joints are provided with flexion angle sensors, so that stimulation of the knee extension muscles for standing or sitting may be carried out under full closed loop control.

It is therefore an object of this invention to provide an apparatus and method for assisting a handicapped person to walk.

Other and further objects of the invention will be apparent from the following description, the accompanying drawings and the appended claims.

BRIEF DESCRIPTION OF THE DRAWINGS

FIG. 1 is a side elevation view of a pair of reciprocating leg braces.

FIG. 2 is a front elevation view of a pair of reciprocating leg braces.

FIGS. 3A through 3D illustrate a sequence of positions achieved by a handicapped person while rising from a sitting to a standing positions.

FIG. 8 is a schematic illustration of the operation of hip control cables.

FIG. 9 is a diagram of a stimulation wave form during walking.

FIG. 10 is a block diagram of a microprocessor system for walking assistance.

FIG. 13 is a front view of an electrode garment.

FIG. 14 is a rear view of an electrode garment.

FIG. 17 is a schematic illustration of a knee flexion sensor.

DESCRIPTION OF THE PREFERRED EMBODIMENTS

Figure 11:
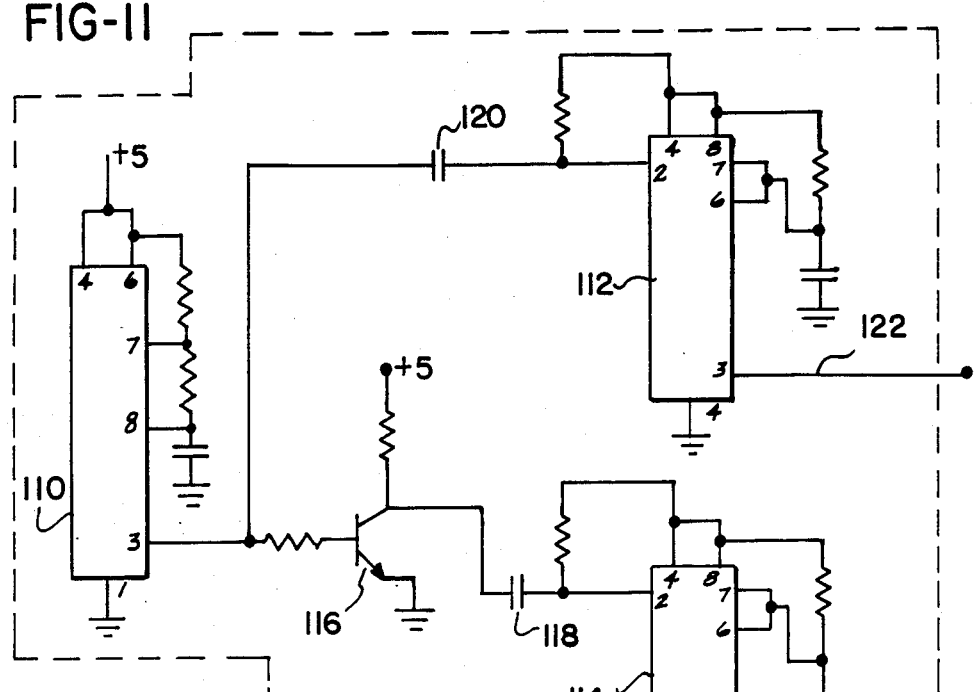
FIG. 11 is a schematic diagram of a pulse generator.
Figure 12:
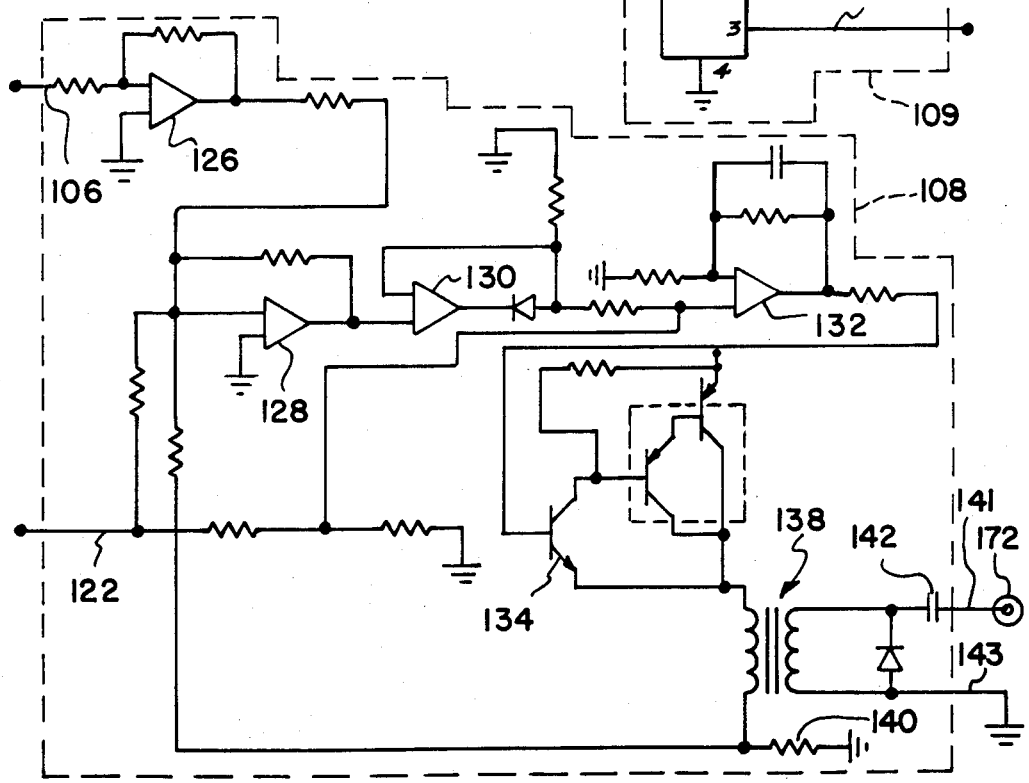
FIG. 12 is a schematic diagram of a stimulation driving circuit.

A walking assistance system in accordance with the present invention comprises a pair of reciprocating braces 20 as illustrated generally in FIGS. 1 and 2 and twelve stimulation circuits 108 as illustrated in FIG. 12. Stimulation pulses generated by stimulation drive circuits 108 are applied to six sets of stimulation electrodes mounted in a fitted garment 166 as illustrated in FIGS. 13 and 14. Stimulation drive circuits 108 modulate pulses provided by six pulse generating circuits 109 as illustrated in FIG. 11 under the control a computer package 72 as illustrated in FIG. 10.

Figure 15:
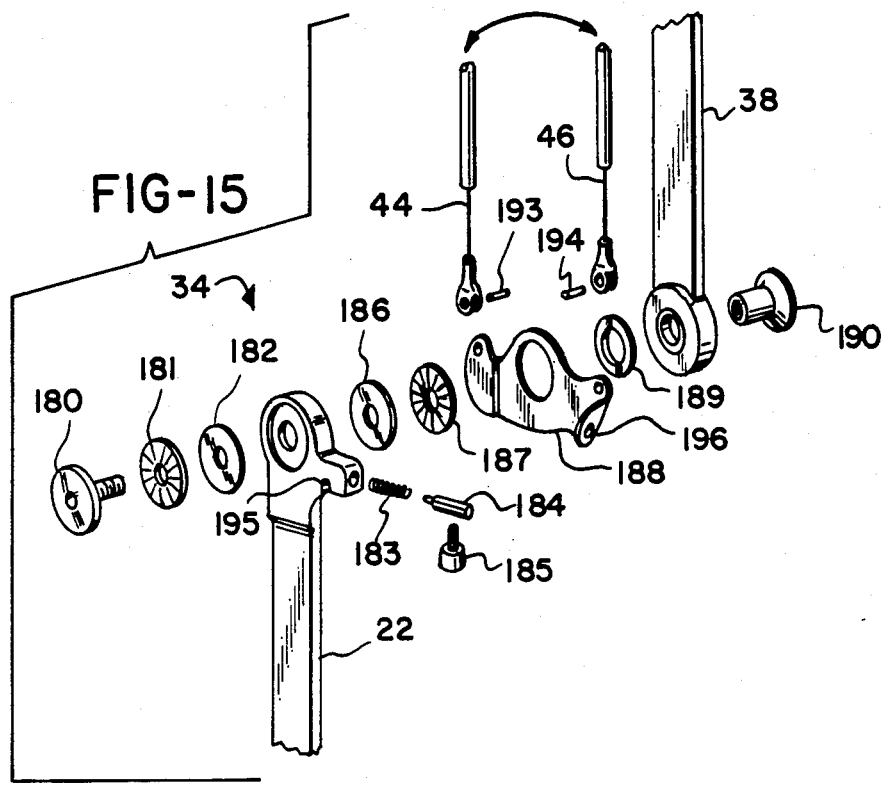
FIG. 15 is an exploded view of a hip joint.

Referring to FIGS. 1 and 2, reciprocating braces 20 comprise left and right upper support rods 22, 24 and left and right lower support rods 26, 28 pivotally joined at left and right knee joints 30, 32. Left and right upper support rods 22, 24 are connected to left and right thoracic extension rods 38, 40 respectively at left and right hip joints 34, 36. Assembly details of one of the hip joints 34, 36 are illustrated in FIG. 15. Braces 20 further comprise a chest strap 42 interconnecting thoracic extension rods 38, 40 and a pelvic band 48 interconnecting hip joints 34, 36. Left and right plastic thigh supports 50, 52 are carried by upper support rods 22, 24 respectively while left and right ankle-foot orthoses (AFOs) 54, 56 are carried by lower support rods 26, 28 respectively. Thigh support 50 and AFO 54 are supported additionally by pivotally joined auxiliary support rods 22a, 26a and thigh support 52 and AFO 56 are additionally supported by pivotally joined auxiliary support rods 24a and 28a. Auxiliary support rods 22a and 24a are not directly connected to hip joints 34, 36.

Figure 7:
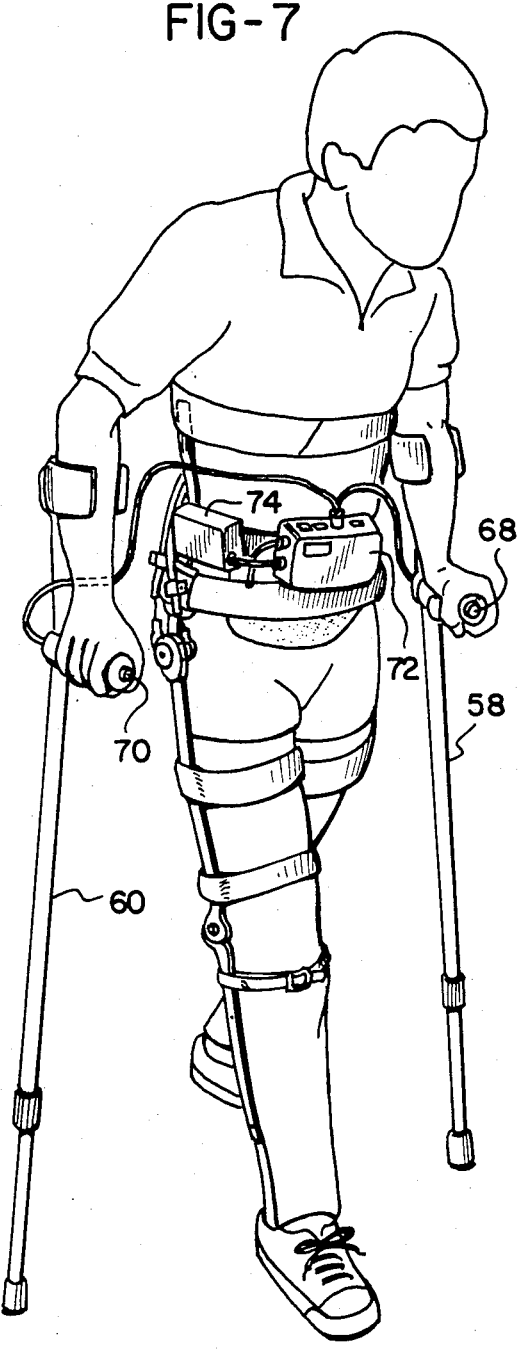
FIG. 7 is a schematic illustration of assisted walking in accordance with the present invention.

Knee joints 30, 32 are provided with releasable locks and with flexion sensors as hereinafter described. For normal walking motion, knee joints 30, 32 are locked at an angle such that the knees of a handicapped wearer are maintained at a slightly off-locked position (3 degrees from full lock) in order to avoid continuous hyperextension. AFOs 54, 56 fit inside the shoes of the wearer in order to support the ankles as generally illustrated in FIG. 7.

Hip joints 34, 36 are interconnected by a forward hip control cable assembly 44 and a rear hip control cable assembly 46 for production of reciprocating leg motion. This motion may be understood by reference to FIG. 8. As illustrated therein assisted walking is performed with cables assemblies 44, 46 engaging support rods 22, 24. The figure specifically illustrates the relative positions of support rods 22, 24 when the handicapped person is being stimulated to move his right leg forward. The stimulation for this movement is applied to the left hamstring and left gluteus maximus muscle groups of the person to cause extension of the left hip. Such left hip extension produces movement of thoracic extension rod 38 and pelvic band 48 in the direction illustrated by arrow 84.

Cable assemblies 44, 46 comprise steel internal cables and plastic outer sheaths (not separately numbered). The sheaths move with thoracic extension rod 38 and pelvic band 48, so that there is relative motion of the internally carried connecting cables as illustrated by the arrows 76, 78, 80 and 82. The backwardly directed extension of the left hip causes relative movement of the cables so as to produce a torque at joint 36 as indicated by the arrow 86. This causes forward motion of support rod 24 and corresponding forward motion of the right leg of the wearer. It will be understood that such forward motion of the right leg is carried out with the weight resting on the left leg and with concomitant closure of a corresponding electrical switch to produce stimulation of the left hip as described above.

It will be apparent that forward motion of the left leg is produced in a similar manner, with the weight resting on the right leg and with stimulation being applied to the right hip. If the weight is applied to the leg opposite the hip being stimulated, then the hip stimulation produces backward movement of the corresponding leg. Thus forward or backward walking motion is achieved. Both types of motion are produced with knee joints 30, 32 locked.

Alternatively, assisted walking in accordance with this invention may be carried out with knee joints 30, 32 alternately unlocked. In that event knee joints 30, 32 preferably are offset joints comprising gravity locks. Such joints are well known in the orthotics field and lock automatically when the knee is fully extended and weight is placed on the leg. Either joint will unlock when the weight is shifted to the other leg and will relock following completion of a step. Reference will now be made to FIG. 15 which illustrates the details of joint 34; joint 36 being similarly designed. The joint includes a joint screw 180 and a nut 190 axially confining a thrust bearing 181, a thrust race 182, a support rod 22, a thrust race 186, a thrust bearing 187, a confining plate 188, a spacer 189, and a thoracic extension rod 38, all in the illustrated relative positions. Cable assemblies 44 and 46 are forwardly and rearwardly joined to confining plate 188 by attachment pins 193, 194 respectively.

Joint 34 also comprises a spring 183, a pin 184 and a locking lever 185, all carried by support rod 22. Locking lever 185 may be located in the position illustrated in FIG. 1 for walking, or, alternatively, may be moved forwardly and upwardly into a detent 195. When locking lever 185 is in its extended position, pin 184 protrudes through aperture 196 in confining plate 188, so that rotation of the confining plate causes corresponding rotation of support rod 22. This effectuates the reciprocating walking motion described above. However, when locking lever 185 is moved into detent 195, pin 184 is disengaged from confining plate 188. When the confining plates at both of hip joints 34, 36 are so disengaged from their associated pins, cables 44, 46 are effectively disengaged from braces 20, and the handicapped person may assume a sitting position.

Figure 4:
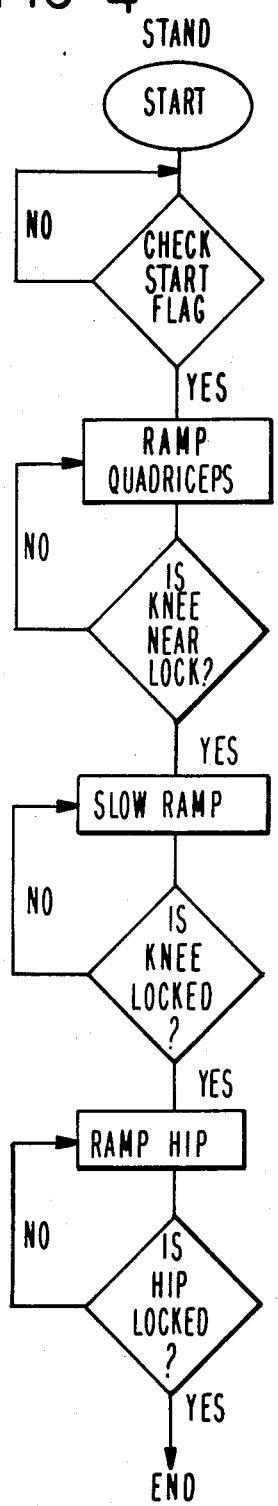
FIG. 4 is a flow chart for a computer routine which controls muscle stimulation during a sitting-to-standing sequence.

Walking in accordance with the present invention may be commenced with a handicapped person wearing a pair of braces 20 and sitting on a chair 62 as illustrated in FIG. 3A. At this time both of hip joints 32, 34 are disengaged and knee joints 30, 32 are unlocked. The handicapped person is also wearing a fitted electrode garment 166, a power pack 74 (FIG. 7) and a computer package 72. When the handicapped person is ready to stand he leans forward as illustrated in FIG. 3B and grasps a pair of crutches 58, 60. He then activates a standing control button 111 (FIG. 10) to initiate a computer routine as generally illustrated by the flow chart of FIG. 4.

As hereinafter described, computer package 72 comprises a Z80 microprocessor. The microprocessor preferably is programmed in 8080 assembly language to produce stimulation and control signals of appropriate magnitude for stimulators 108. A complete program listing for a similar computer program is set forth in Petrofsky U.S. Application Ser. No. 561,720 filed Dec. 15, 1983, and the disclosure of that application is hereby incorporated herein. Reference may be made to that application for an understanding of programming techniques appropriate to implement the routines set forth throughout this application in flow chart form. It will be appreciated that other microprocessors and other programming languages may be employed. It is important only that the computer generate six control signals representing the amount of stimulation desired for the left and right gluteus maximus, hamstring and quadriceps muscle groups. Additional or different muscles groups, may be stimulated to produce the movements described herein.

After the handicapped person has activated standing control button 111, the computer causes application of ramped control signals to electrodes positioned for stimulation of both the left and right quadriceps muscles. During this ramping action, the computer monitors the flexion angles for both knees, as provided by feedback sensors which may be simple potentiometers positioned at knee joints 30. 32 Alternatively, the flexion angle sensors may be strain gauge devices as hereinafter described with reference to FIG. 17. Stimulated extension of both knees proceeds under full closed loop control until the feedback sensors indicate that the knees are near a locked position. At this point, the ramps are slowed down, and the computer begins looking for signals from micro-switches 115, 117 (FIG. 10) indicating that a knee-lock condition has been achieved. Knee joints 30, 32 are locked into position when a knee-lock condition has been achieved. At this time, the handicapped person has assumed a posture as generally illustrated in FIG. 3C.

After knee-lock has been achieved, the computer applies a ramp signal to the left and right gluteus maximus muscle groups and also to the left and right hamstring muscle groups. This causes simultaneous extension of both hips, so that the handicapped person assumes the posture illustrated in FIG. 3D. Ramping of the hip extension muscles proceeds on an open loop basis until micro-switches 119 amd 121 at the left and right hips respectively indicate that an erect posture has been achieved. The computer then maintains stimulation at a constant level while the handicapped person manually engages locking levers 185 in both of hip joints 34, 36, at which time cable assemblies 44, 46 maintain an erect body posture without computer stimulation.

The above described ramp signal is generated in accordance with a routine which causes an exponential increase in stimulation voltage for progressively larger errors in the knee position away from lock. For any large change in stimulation voltage, proportional software time lags are introduced. This allows for time lags in physiological response to stimulation. It has been found that the body has an inherent time lag of about 100 milliseconds in responding to stimulation, and software time lags are necessary in order to avoid unstable oscillation.

Figure 5:
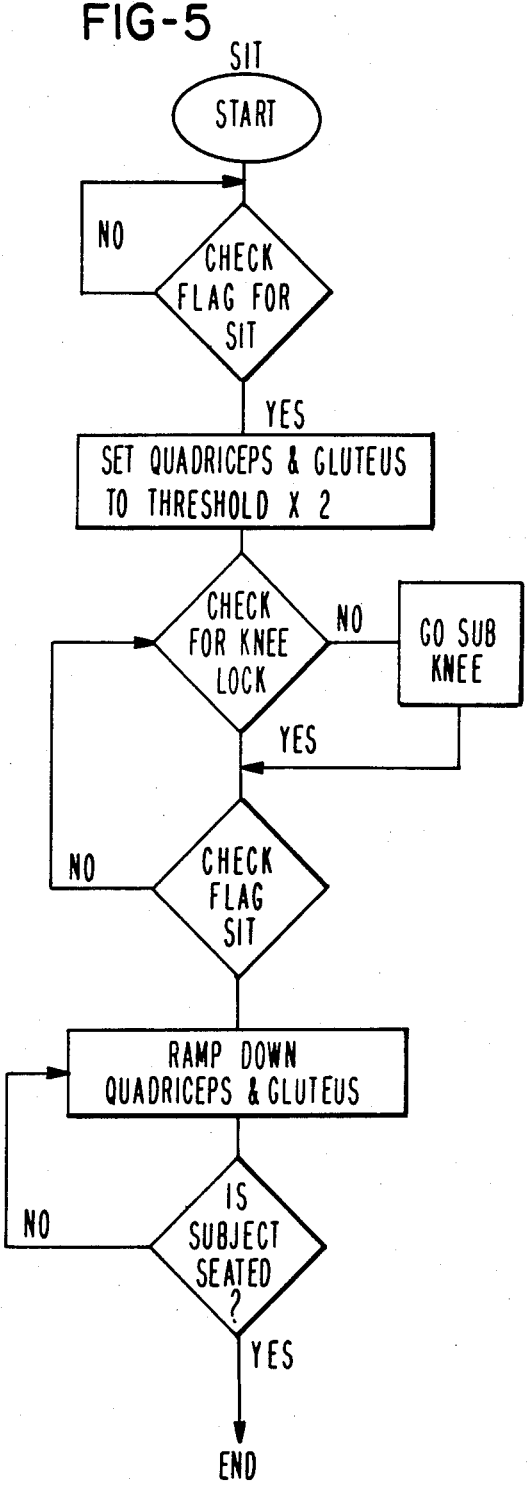
FIG. 5 is a flow chart for a computer routine to generate stimulation control signals for a standing-to-sitting sequence.

Computer controlled sitting proceeds as outlined by the flow chart of FIG. 5. The sequence is initiated by manual activation of a sitting control button 113. Once this button has been activated the computer stimulates the quadriceps and gluteus maximus muscles for extending the knee and hip joints to maintain an erect body posture. At this point the handicapped person unlocks the knee joints, disengages the hip joints and pushes button 113 a second time to signal the computer that sitting may commence. Thereafter the computer ramps down the quadriceps and gluteus maximus muscles until the person is seated.

Figure 6:
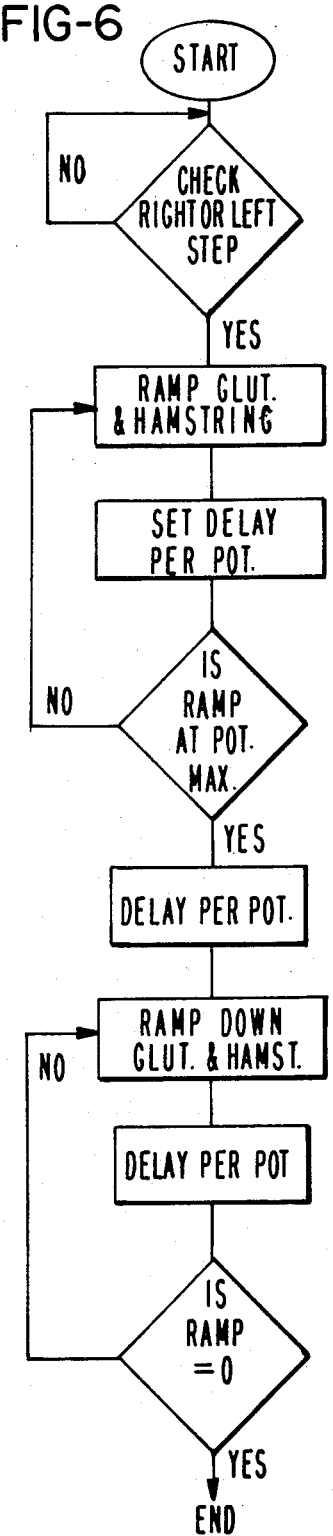
FIG. 6 is a flow chart for a computer routine to stimulate extension of a hip for walking assistance.

Walking proceeds in accordance with the flow chart illustrated in FIG. 6 and under the control of control buttons 58, 60. When the handicapped person desires to move his right leg forward, he places his weight on his left leg and activates control button 68. This causes extension of his left hip and concomitant forward movement of his right leg as described above. Thereafter the weight is placed on the right foot and control button 70 is activated to cause forward movement of the left leg. During the walking routine outlined by FIG. 6, the knee joints remain locked and only the hamstring and gluteus maximus muscles are stimulated to produce alternating movement of the legs.

For walking in accordance with the alternative embodiment of the invention the handicapped person again shifts his weight and operates buttons 58, 60 as above described. However, the computer reacts to operation of a control button by first stimulating the hamstring muscles for the nonweight bearing leg. The weight shifting unlocks that knee, and the hamstring stimulation flexes it. Thereafter stimulation is applied to the hamstring and gluteus maximus muscles for the weight bearing hip. This extends that hip and causes forward movement of the leg which has just been flexed at the knee. At the end of such forward movement, the quadriceps muscles for the forwardly moving leg are momentarily stimulated to extend the knee and cause locking of the joint when the foot of that leg strikes the ground. The assisted person then shifts his weight to that leg and operates the opposite button. This instructs the computer to repeat the sequence (with left-to-right reversal) for the next step.

The stimulation wave form utilized for walking is illustrated in FIG. 9, as designated by the reference numeral 88. The wave consists of a slow ramp up, a plateau and a slow ramp down. The amplitude of the wave is determined by a potentiometer 101 connected to an analog digital converter 98 (FIG. 10). The period of the wave is controlled by a second potentiometer 105 also connected to analog-to-digital converter 98. The amplitude of the wave controls the strength of the muscle contractions and the speed of leg movement while the period of the wave controls the duration of the muscle contractions and the duration of the steps.

Computer package 72 is built around a microprocessor 90 connected as generally illustrated in FIG. 10. As noted above, microprocessor 90 may be a Z80 microprocessor. Connections for microprocessor 90 are similar to the connections described in Ser. No. 561,720, and reference may be made to that application for a full understanding thereof. For purposes of this application a general block diagram as set forth in FIG. 10 is believed sufficient. Accordingly, microprocessor 90 reads a control program stored in EPROM 94 and operates in collaboration with a RAM 92. A series of parallel ports 96 provide binary inputs from a series of control switches 68, 70, 111, 113, 115, 117, 119 and 121 and binary outputs to a series of LEDs, not illustrated. Analog signals representing knee flexion angles fed back from the knee flexion sensors are applied to ADC 98 via lines 104. ADC 98 digitizes these signals as well as the signals from potentiometers 101 and 105 for processing by microprocessor 90. In response thereto microprocessor 90 provides six sets of stimulation control signals to six digital-to-analog converters 100 for application to six lines 106.

Stimulation driving signals in analog form are applied via lines 106 to stimulation drive circuits 108, as illustrated in FIG. 12. As noted above, there are twelve such stimulation driving circuits 108. Two stimulation driving circuits 108 are required for each stimulated muscle group, and those drive circuits are commonly connected to the same control line 106.

For each pair of stimulation drive circuits 108 there is a common pulse generating circuit 109, as generally illustrated in FIG. 11. These pulse generating circuits generate alternating 300 microsecond pulses on output lines 122, 124 for application to the corresponding stimulation driving circuits 108.

Pulse generating circuit 109 comprises three NE555 timers 110, 112 and 114. Timer 110 is used as a free running oscillator at a frequency of 40 Hz. The output of this timer triggers timers 112 and 114. Timers 112 and 114 are triggered via 0.001 microfarad capacitors 120 and 118 respectively. The trigger signal for timer 114 is also inverted by a 2N3904 transistor 116. The resulting 300 microsecond pulses on lines 122, 124 each occur at a frequency of 40 Hz and are 180 degrees out of phase with each other. These pulses are amplitude modulated by stimulation driving circuits 108 in accordance with the amplitude of the signal appearing on control line 106. A pair of cooperating stimulation drive circuits 108 produce a balanced-biphasic current controlled stimulation signal which is applied to a group of three electrodes for stimulation of a single muscle group.

Stimulation driving circuit 108 comprises four operational amplifiers 126, 128, 130 and 132, each of which may be an LF353N integrated circuit. These four amplifiers modulate the pulses provided on input line 122. The output from the fourth amplifier 132 is provided to a driving transistor 134 which may be a 2N3904 device. The output of driver 134 is provided to a D45E2 Darlington transistor, which in turn drives an RF isolation transformer 138. The output of transformer 138 is applied via a 1.0 microfarad capacitor 142 to an output line 141. The other line 143 of the transformer secondary is connected to an RF ground. This RF ground is also connected to one electrode of the electrode set controlling stimulation of a single muscle group and to the secondary side of the cooperating stimulation driving circuit 108. This then explains the use of a set of three electrodes for stimulation of a single muscle group. Further background information may be obtained by reference to Petrofsky et al U.S. Pat. No. 4,492,233 the disclosure of which patent is hereby incorporated herein.

As further illustrated in FIG. 12, there is a 0.1 ohm resistor 140 in series with the primary of transformer 138. This resistor serves three functions. Firstly, it serves as a sense resistor to provide a current feedback for the operational amplifier circuit. Secondly, it enables generation of pulses which are cut off when one of the stimulation electrodes becomes opened. This provides a safety factor to protect subjects from burns. Thirdly, resistor 140 serves as a fuse. In the event that Darlington transistor 142 goes into a thermal runaway condition a DC bias is placed across transformer 138. This "blows" resistor 140 thereby avoiding overbiasing of the circuit and delivery of excess current.

Capacitor 142 in cooperation with a similar capacitor 142 in the corresponding paired driving circuit produces a balanced biphasic current. Preferably the current ranges from about 1 milliamphere to about 400 milliamperes. This can be adjusted by replacing resistor 140 with another resistor of a different value.

Stimulation signals from stimulation drive circuits 108 may be applied to sets of transcutaneous electrodes attached to the skin of the handicapped person as generally described in Petrofsky et al U.S. Pat. No. 4,492,233. Alternatively the stimulation signals may be applied to a set of stimulation electrodes incorporated into a garment 166, as generally illustrated in FIGS. 13 and 14.

The garment 166 may have two sets of electrodes 172 interiorly mounted in the legs thereof, as illustrated in FIG. 13. Garment 166 maintains electrodes 172 in position against the skin of the handicapped person in predetermined patterns above the quadriceps muscle groups. Lead lines from electrodes 172 extend upwardly to a common connector 168 positioned in the area of the waistband 170. As illustrated in FIG. 14, garment 166 also has two sets of stimulation electrodes 174 mounted posteriorly for positioning against the skin above the gluteus maximus muscles and two sets of electrodes 176 posteriorly mounted for positioning against the skin above the hamstring muscles. Electrodes 174 and 176 also have lead lines extending forwardly and upwardly for connection to common connector 168. Connector 168 in turn is connected to computer package 72.

The details of one embodiment of a knee flexion sensor 144 are illustrated in FIG. 17. Flexion sensor 144 comprises a spring 162 extended between an upper torsion bar 146 and a lower torsion bar 148. Bending of the knee extends spring 162, thereby applying a load to upper torsion bar 146 and a strain gauge 150 mounted thereon. Strain gauge 150 provides a signal on line 104 which may be interpreted by microprocessor 90 as a flexion angle. The knee joint is also provided with a microswitch 117 operated by a switch arm 154 to provide a signal on line 102 when a knee lock condition has been achieved. As illustrated in FIG. 10, there is another microswitch 115 for sensing knee-lock in the opposite leg.

Figure 16:
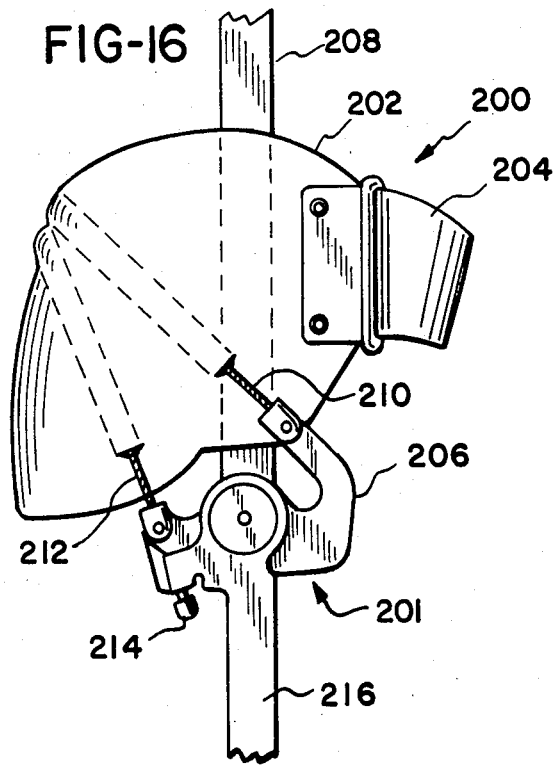
FIG. 16 is a drawing of a pelvic attachment in an alternative embodiment.

FIG. 16 illustrates an alternative embodiment of a pelvic attachment for reciprocating braces 20. The alternative attachment 200 comprises a plastic pelvic band 202 and anterior strap 204. A forward cable 210 and a rear cable 212, functionally equivalent to the above described cables 44 and 46 respectively, are confined within pelvic bands 202. Cables 210 and 212 are attached to a confining plate 206 for detachable connection to upper support rod 216. A locking lever 214 is provided for detachment of confining plate 206 from support rod 216. Thoracic strap 208 is freely pivoted about support rod 216.

It will be appreciated that the leg braces of the present invention restrict the legs of the wearer to forward and rearward movement. It will also be appreciated that braces 20 may be of very light weight construction through use of plastic and graphite strips and may be substantially concealed beneath loose fitting outer clothing of the wearer.

The set of stimulation electrodes 174 which stimulate the left gluteus maximus muscles and the set of stimulation electrodes 176 which stimulate the left hamstring muscles, together with their associated stimulation driving circuit 108 and pulse generating circuits 109 are component parts of a first stimulation means for stimulating controlled contraction of the left hip extension muscles. Similarly, the stimulation electrodes 174 which stimulate the right gluteus maximus muscles and the stimulation electrode 176 which stimulate the right hamstring muscles, together with their associated stimulation driving circuits 108 and pulse generating circuits 109 are component parts of a second stimulation means for stimulating controlled contractions of the right hip extension muscles.

Those stimulation electrodes 172 which stimulate the left quadriceps muscles, together with their associated stimulation driving circuit 108 and pulse generating circuit 109 are component parts of a third stimulation means for stimulating controlled contractions of the left knee extension muscles. The electrodes 172 which stimulate the right quadriceps muscles, together with their associated stimulation driving circuits 108 and pulse generating circuit 109 are component parts of a fourth stimulation means for stimulating controlled contractions of the right knee extension muscles. The feedback sensors at knee joints 30 and 32 are component parts of first and second sensing means for sensing the flexion angles of the left and right knees respectively.

Either of cable pairs 44, 46 or 210, 212 will be understood to constitute interconnection means for causing forward movement of either left or right leg braces in response to extension of the opposite hip of a wearer. Control buttons 68, 70 and computer package 72 are component part of a control means for selective activation to cause alternate operation of the first and second stimulation means.

While the methods and forms of apparatus herein described constitute preferred embodiments of this invention, it is to be understood that the the invention is not limited to these precise forms of application, and that changes may be made therein without departing from the scope of the invention which is defined in the appended claims.

What is claimed is:

1. A walking assistance system comprising:
   left and right leg braces for supporting a handicapped person in a standing position, said braces being configured for restricting the legs of said person to forward and rearward movement,
   interconnection means for causing forward movement of a nonweight bearing one of said braces in response to extension of a weight bearing opposite hip of said person
   first and second stimulation means for stimulating controlled contractions of the left and right hip extension muscles respectively of said person, and
   control means for selective activation by said person to cause alternate operation of said first and second stimulation means and resultant steps defining a walking motion.

2. Apparatus according to claim 1, said control means comprising means for activation by said person to adjust the speed and duration of said steps.

3. Apparatus according to claim 1, said braces comprising joints for permitting flexion and extension of the knees and locking means for selectively locking said knees at predetermined flexion angles.

4. Apparatus according to claim 3 wherein said knee joints are offset and comprise gravity locks.

5. Apparatus according to claim 3 further comprising:
   third and fourth stimulation means for stimulating controlled contractions of the left knee and right knee extension muscles respectively of said person, said control means comprising computing means for causing said third and fourth stimulation means to produce a simultaneous controlled contraction of said knee extension muscles and also causing said first and second stimulation means to produce a coordinated contraction of both of said hip extension muscles, so that said person rises from a sitting position to a standing position.

6. Apparatus according to claim 5 and further comprising first and second sensing means for sensing the flexion angles of the left and right knees respectively of said person;
   said computing means being responsive to said first and second sensing means for closed loop control of said contractions.

7. Apparatus according to claim 5 and further comprising means for sensing hip flexion angles indicating an erect posture and means for communicating said indication to said computing means.

8. Apparatus according to claim 1 wherein said interconnection means include means for causing rearward movement of a nonweight bearing one of said braces when the weight of said person is placed on the opposite leg and the nonweight bearing hip of said person is extended.

9. Apparatus according to claim 8 wherein said left and right braces each comprise hip joints and said interconnecting means comprises a pair of cables for producing cooperative torques at said joints.

10. A method of assisting a seated handicapped person to rise and walk comprising the steps of:
   restricting the legs of said person to forward and rearward movement,
   simultaneously stimulating the extension muscles for both knees of said person to produce a rising motion,
   simultaneously stimulating the extension muscles for both hips of said person to produce an erect standing position, mechanically interconnecting the hips of said person so that supported extension of one hip produces flexion of the other, and alternately stimulating said hip extension muscles to produce opposite hip flexion and a resultant walking sequence;

said person participating in such method by leaning forward from an initial sitting position and by alternately shifting his weight from hip to hip during said walking sequence.

11. A method according to claim 10 and further comprising the step of locking said knees in a substantially fully extended position whenever they are bearing weight during said walking sequence.

12. A method according to claim 11 and further comprising the steps of unlocking and flexing said knees during flexion of their corresponding hips.

* * * * *

UNITED STATES PATENT AND TRADEMARK OFFICE
CERTIFICATE OF CORRECTION

PATENT NO. : 4,697,808

DATED : October 6, 1987

INVENTOR(S) : Paul F. Larson, Roy D. Douglas, Jerrold S. Petrofsky, Chandler A. Phillips It is certified that error appears in the above-identified patent and that said Letters Patent is hereby corrected as shown below:

Column 10, Line 22, after "knees" insert --of said person--.

Signed and Sealed this

Seventeenth Day of April, 1990

Attest:

HARRY F. MANBECK, JR.

*Attesting Officer*   *Commissioner of Patents and Trademarks*